United States Patent [19]

Thomas et al.

[11] Patent Number: 5,175,271
[45] Date of Patent: * Dec. 29, 1992

[54] USE OF SILICA GEL FOR DNA EXTRACTION WITH ORGANIC SOLVENTS

[75] Inventors: Stanley Thomas; Lowell Tilzer; Ruben Moreno, all of Overland Park, Kans.

[73] Assignee: University of Kansas, Kansas City, Kans.

[*] Notice: The portion of the term of this patent subsequent to Apr. 21, 2009 has been disclaimed.

[21] Appl. No.: 825,695

[22] Filed: Jan. 27, 1992

Related U.S. Application Data

[63] Continuation of Ser. No. 381,588, Jul. 10, 1989, Pat. No. 5,106,966.

[51] Int. Cl.⁵ .................... C07H 21/00; C07H 21/04
[52] U.S. Cl. .................................. 536/27; 536/28; 536/29; 536/127; 435/6; 435/803
[58] Field of Search .................... 536/27; 435/6, 267, 435/274

[56] References Cited

U.S. PATENT DOCUMENTS

| | | | |
|---|---|---|---|
| 4,833,239 | 5/1989 | DeBonville et al. | 536/27 |
| 4,921,952 | 5/1990 | Longmire et al. | 536/27 |
| 4,923,978 | 5/1990 | McCormick | 536/27 |
| 5,106,966 | 4/1992 | Thomas et al. | 536/27 |

Primary Examiner—Johnnie R. Brown
Assistant Examiner—Gary L. Kunz
Attorney, Agent, or Firm—Felfe & Lynch

[57] ABSTRACT

The invention describes a method for extracting DNA from a sample. It involves contacting a sample with a separation reagent which permits differentiated solvation of DNA and protein. By adding a gel polymer, such as a silical gel polymer to the mixture of sample and separating reagent followed by agitation via, e.g., centrifugation, the DNA and protein are separated, with the gel acting as a block to prevent contamination of the DNA phase by the protein. Higher yields of DNA are obtained as compared to methodologies where the gel is not used. Additionally, the problems associated with the physical contact of the solvents, which are frequently carcinogens, are avoided. Also taught are kits which can be used in connection with the inventive method.

9 Claims, 2 Drawing Sheets

USE OF SILICA GEL FOR DNA EXTRACTION WITH ORGANIC SOLVENTS

RELATED APPLICATION

This is a continuation of U.S. patent application Ser No. 07/381,588, filed Jul. 10, 1989, now U.S. Pat. No. 5,106,966.

FIELD OF THE INVENTION

This invention relates to methods and reagents useful in separating DNA from samples which contain it.

BACKGROUND AND PRIOR ART

In many applications of biological and biochemical research, it is important or essential to obtain purified DNA from samples. Frequently, an investigator must obtain a pure sample of plasmids or nuclear DNA, e.g., in assaying for genes which express a particular protein, to determine whether or not a particular sample of cell has been transfected by a foreign gene, and so forth.

The standard methodology for extracting DNA, as explained, e.g., by Herrmann, et al., Meth. Enzymol 152: 180–183 (1987), involves differentiated solvation of the DNA and the non-DNA material, using phenol and chloroform. In this standard methodology, following a series of preparative steps the DNA containing sample is mixed with an organic solvent, such as phenol, or preferably, an equal mixture of phenol and chloroform. Proteins denature and enter the organic phase (phenol), or precipitate at the interface of the organic and aqueous phases. The aqueous phase contains the DNA. Mixing this with alcohol causes precipitation of the DNA which can then be spooled. See, e.g., Rodriquez, et al., Recombinant DNA Techniques: An Introduction (Benjamin/Cummings Publishing Co., Menlo Park, 1983), pg. 38.

While the aforementioned phenol/chloroform extraction method is standard in the art, it is far from ideal. Phenol and chloroform are both toxic chemicals, implicated as potential carcinogens, so it is of course desirable that the investigator not contact these. However, the standard protocols for separation require aspiration of the aqueous DNA containing solvent. Pouring the material from the second solvent is not an acceptable alternative, because the barrier between phenol and chloroform is not very stable, and contamination is inevitable. Further, at the interphase between the chloroform and phenol layers, it frequently becomes very difficult to separate the DNA found at this point. As a result, yields are low, or, at the least, not as high as they can be.

Thus, it is desirable to have available a method which permits the investigator to carry out DNA extraction and/or separation which does not require aspiration. Further, it is desirable to have a method available which, in addition to being safe to us, results in high yields of DNA.

SUMMARY OF THE INVENTION

The invention is a method for separating DNA from a sample containing it, via the use of differentiated solvents and silica gel. It has been found surprisingly, that when a receptacle containing a gel barrier, such as a silica gel, on the bottom of its interior has added thereto a sample containing DNA and a separation reagent, following agitation such as by, e.g., centrifugation, the silica gel moves in the sample and acts to separate the aqueous solvent and the organic solvent from each other. The silica then acts as a "block", permitting the decanting of the aqueous solvent containing the DNA from the rest of the mixture. This means that aspiration of the solvent is not necessary, and the rest of contamination by either of phenol or chloroform, e.g., is eliminated. It has also been found that this method results in unexpectedly high yields of DNA.

Also encompassed by this invention is a kit for use in DNA extraction, the components of which comprise a separation reagent which allows extraction of the DNA into a solvent and away from non-DNA containing materials, an amount of, gel sufficient for extractions, and a receptacle means, such as a glass tube, for holding the sample, separation reagent, and silica. These distinct elements of the kit are joined by a container means, such as a box.

DETAILED DESCRIPTION OF PREFERRED EMBODIMENTS

Figure 1:
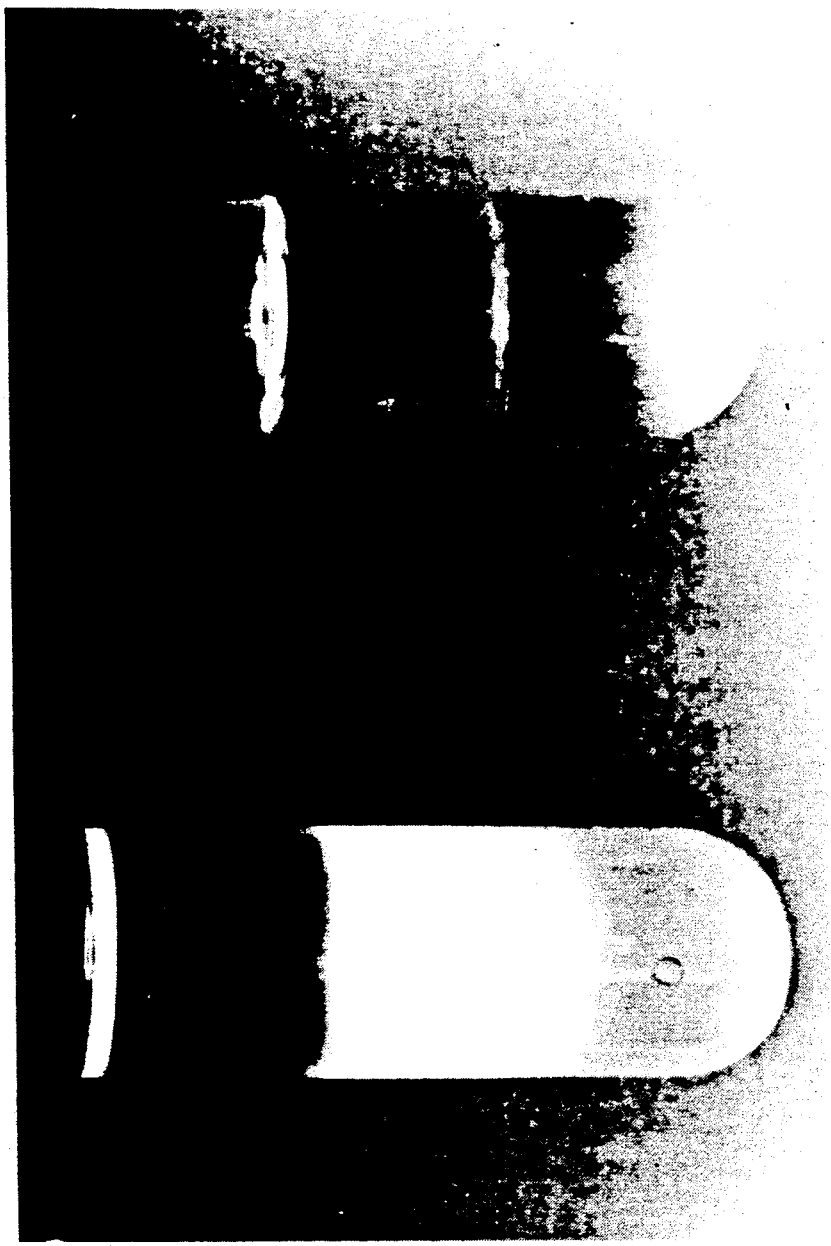
FIG. 1 shows comparative extraction in glass tubes using either polyester gel (FIG. 1a), or no gel (FIG. 1b).

As used herein, "separation reagent" refers to any reagent which permits one to separate DNA from a sample containing it. Typically, this is a phenol-chloroform mixture. Other reagents may be used, such as cesium chloride gradient solutions, or other types of salt gradients.

"Receptacle" refers to any container means which can be used to hold a sample solution. Most preferably, these are small glass tubes, such as those used for serum separation.

"Agitation" refers to any process which serves to mix the sample and the separation reagent so as to permit the DNA to dissolve into the aqueous portion thereof. Most preferably, the agitation takes the form of centrifugation, but other types of agitation, such as shaking, are envisioned as well.

EXAMPLE

White blood cell nuclei were isolated from 5 to 7 ml of EDTA anticoagulated whole blood by the method of Min, et al., Br. J. Hematol. 68: 195–201 (1988). The isolated nuclei were resuspended in 2.0 ml of 20 mM Tris pH 7.4 and 150 mM NaCl. One ml of 400 mM Tris pH 8.0, 100 mM EDTA, and 1% sodium dodecyl sulfate containing 100 micrograms of Proteinase K (Oncor, Gaithersburg, Md.) was added and the mixture incubated 1 hour at 60° C. The digest was extracted with an equal volume of phenol:chloroform: isoamyl alcohol (24:24:1) for five minutes within a Becton Dickinson (Rutherford, N. J.) Serum Separator tubes containing the polyester gel polymer. The tube was sealed very tightly permitting no leakage of contents during the mixing procedure. The tube was centrifuged 5 minutes at room temperature at 1000 g. The aqueous phase was then poured into another gel containing tube for further organic solvent extraction or precipitated with one half volume of 7.5 M ammonium acetate and two and one half volumes of 100% ethanol. If the aqueous phase was further purified it was don by mixing with fresh phenol:chloroform:isoamyl-alcohol or chloroform:isoamyl-alcohol alone. The precipitated DNA was spooled and then resuspended in 0.2–0.5 ml of 10 mM Tris pH 7.4 containing 1 mM EDTA.

DNA was incubated overnight at 50° C. after which the solutions were read spectrophotometrically at 260 and 280 nm wavelengths. The DNA was digested with various restriction endonucleases as suggested by the manufacturer (Bethesda Research Laboratories, Gaithersburg, Md.). Five micrograms of digested DNA were loaded onto 0.7% agarose gels and electrophoresed for 16 hours 2.0 volts per cm. The gels were stained with ethidium bromide and examined with ultraviolet light.

FIG. 1 compares a typical extraction with and without polyester gel polymer tubes. The tube on the left was extracted with polyester gel while the tube on the right contained no gel. Before centrifugation the gel was located at the bottom of the tube. After centrifugation, the polyester polymer moved between the aqueous and organic layers. The protein was located beneath the gel layer, far from the aqueous DNA containing phase.

Figure 2:
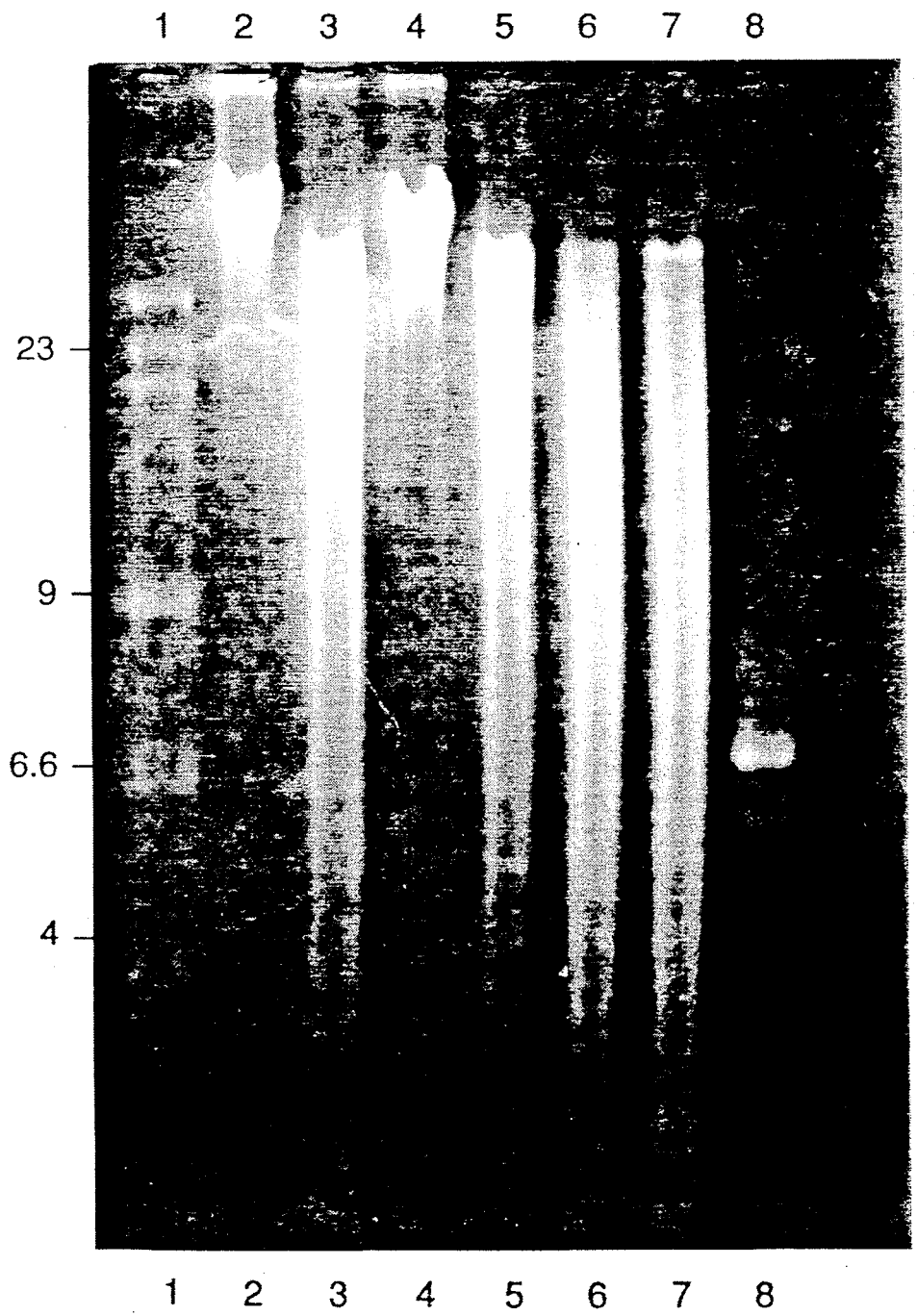
FIG. 2 shows gel electrophoresis patterns for DNA extracted either using standard methods, (lanes 2 and 3), or the methodology of the invention (lanes 5–8).

Table 1, which follows, shows that the DNA extracted with the polyester polymer method produced almost 40% more DNA compared with the usual method without gel. The relative purity of the extraction was revealed by the $A_{260}/A_{280}$. The absorbance ratio of the preparations purified with the polyester gel was consistently 1.8, suggesting absence of protein contamination. Maniatis, et al., *Molecular Cloning. A laboratory Manual* (Cold Spring Harbor Laboratory, Cold Spring Harbor) (1981). Finally, the quality of the DNA extracted with the polyester polymer method was illustrated by restriction endonuclease digestion. The polyester polymer prepared DNA digested as expected with BamHI, EcoRI, and HindIII restriction endonucleases (FIG. 2, lanes 5–7), and had the same appearance after electrophoresis when compared with the standard technique (FIG. 2, lane 3). There were no differences in DNA extracted by standard or polyester gel procedure with Southern blots and routine hybridizations (results not shown). In addition, the procedure allowed phenol-chloroform extraction after plasmid purification (FIG. 2, lane 8).

TABLE 1

|  | $A_{260}$ nnm | Quantity ug/ul |
|---|---|---|
| Sample 1 Standard | 0.051 | 0.255 |
| Polyester gel | 0.070 | 0.350 |
| Sample 2 Standard | 0.070 | 0.370 |
| Polyester | 0.088 | 0.440 |
| Sample 3 Standard | 0.060 | 0.300 |
| Polyester | 0.107 | 0.535 |
| Sample 4 Standard | 0.058 | 0.290 |
| Polyester | 0.074 | 0.370 |
| Sample 5 Standard | 0.054 | 0.270 |
| Polyester | 0.080 | 0.400 |
| Sample 6 Standard | 0.050 | 0.250 |
| Polyester | 0.074 | 0.360 |

These results show that separation of DNA from a sample can be accomplished without the previously accepted methodologies requiring the investigator to contact the solvents. The described method permits attainment of higher yields of DNA than those obtained using standard phenol/chloroform extraction protocols.

The described method is useful, in addition, in extraction of DNA from small number of cells using microcentrifuge tubes containing gel polymers. This is important when a small amount of sample is all that is available. This is of particular relevance in situations such as "DNA fingerprinting" where a forensic sample is used, which may be very small and of poor quality.

The method can also be adapted for other methods of DNA separation, such as non-organic salting out, as exemplified by, e.g., Miller, Nucl. Acids. Res. 16: 1215 (1986). In the adaptation of the salting out method via the techniques described herein, the protein components are trapped within the gel, again allowing the investigator to decant the aqueous, DNA containing phase without protein contamination.

The terms and expressions which have been employed are used as terms of description and not of limitation, and there is not intention in the use of such terms and expressions of excluding any equivalents of the features shown and described or portions thereof, it being recognized that various modifications are possible within the scope of the invention.

We claim:

1. In a method for isolating and purifying DNA from a biological sample, comprising:
   (i) contacting said sample with (a) a first aqueous saline solution and (b) with an aqueous immiscible organic solvent to form a mixture, and agitating said mixture to separate DNA into said first solution, the improvement comprising:
   (ii) adding a silica gel polymer to said mixture prior to agitating it, wherein said gel polymer moves in said mixture to separate said DNA containing first solution from said immiscible organic solvent, and
   (iii) decanting DNA containing aqueous saline from said aqueous immiscible organic solvent, wherein said immiscible organic solvent contains protein.

2. Method of claim 1, wherein said first solvent comprises an aqueous saline solution containing detergent and a protease and said second solvent comprises chloroform and phenol.

3. Method of claim 2, wherein said solvent further comprises isoamyl alcohol.

4. Method of claim 1, wherein said DNA comprises nuclear DNA.

5. Method of claim 1, wherein said sample is a whole cell sample.

6. Method of claim 1, wherein said DNA is plasmid DNA.

7. Kit useful in separating DNA from a biological sample comprising:
   (i) a separation reagent containing;
      (ia) a first aqueous saline solvent which extracts DNA from a biological sample;
      (ib) a second aqueous-immiscible, organic solvent which extracts non-DNA components from a biological sample;
   (ii) a silica gel polymer in an amount sufficient to separate DNA containing first solvent from non-DNA containing second solvent wherein said gel polymer moves in the presence of said first and second solvents to separate them from each other;
   (iii) a receptacle means for receipt of the sample, separation reagent and gel polymer; and
   (iv) a container means for holding items (i), (ii) and (iii).

8. Kit of claim 7, wherein said first solvent comprises an aqueous solution of detergent and a protease, and said second solution comprises phenol and chloroform.

9. Kit of claim 7, wherein said second solvent further comprises isoamyl alcohol.

* * * * *